United States Patent
Villette

(10) Patent No.: US 6,354,603 B1
(45) Date of Patent: Mar. 12, 2002

(54) SEALING DEVICE FOR CARPULE

(76) Inventor: Alain Villette, Les Vannes, F-79700 St Pierre des Echaubrognes (FR)

( * ) Notice: Subject to any disclaimer, the term of this patent is extended or adjusted under 35 U.S.C. 154(b) by 0 days.

(21) Appl. No.: 09/486,874

(22) PCT Filed: Feb. 7, 1999

(86) PCT No.: PCT/FR99/01588
§ 371 Date: May 5, 2000
§ 102(e) Date: May 5, 2000

(87) PCT Pub. No.: WO00/01430
PCT Pub. Date: Jan. 13, 2000

(30) Foreign Application Priority Data

Mar. 7, 1998 (FR) .............................................. 98 08503

(51) Int. Cl.[7] .............................. A61M 5/00; F16J 15/02
(52) U.S. Cl. ...................... 277/637; 277/644; 604/232; 604/240; 604/414; 215/350; 215/DIG. 3
(58) Field of Search ................................. 277/634, 637, 277/644; 604/232, 240, 242, 414; 215/349, 350, 351, DIG. 3

(56) References Cited

U.S. PATENT DOCUMENTS

| | | | |
|---|---|---|---|
| 1,993,629 A | | 3/1935 | Smith |
| 2,157,503 A | | 5/1939 | Smith |
| 2,870,766 A | * | 1/1959 | Dann et al. |
| 3,084,688 A | * | 4/1963 | McConnaughey |
| 3,387,609 A | * | 6/1968 | Shields ........................ 604/202 |
| 3,710,794 A | * | 1/1973 | Shields ......................... 123/218 |
| 3,976,069 A | * | 8/1976 | Ong ............................. 123/218 |
| 3,995,630 A | * | 12/1976 | van de Veerdonk ........ 123/218 |
| 4,568,346 A | * | 2/1986 | van Dijk ..................... 604/414 |
| 4,909,794 A | * | 3/1990 | Haber et al. ................. 604/195 |
| 4,935,014 A | * | 6/1990 | Haber .......................... 604/195 |
| 4,982,769 A | * | 1/1991 | Fournier et al. .............. 141/98 |
| 5,067,945 A | * | 11/1991 | Ryan et al. .................. 604/198 |
| 5,085,332 A | * | 2/1992 | Gettig et al. ................. 215/249 |
| 5,188,599 A | * | 2/1993 | Botich et al. ................ 604/110 |
| 5,316,163 A | * | 5/1994 | von Schuckmann ........ 215/249 |
| 5,334,162 A | * | 8/1994 | Harris ......................... 604/232 |
| 5,421,469 A | * | 6/1995 | Lee ............................. 215/274 |
| 5,611,786 A | * | 3/1997 | Kirchhofer et al. ......... 604/240 |
| 5,662,230 A | * | 9/1997 | Finneran ..................... 215/252 |
| 5,709,668 A | * | 1/1998 | Wacks ......................... 604/232 |
| 5,718,690 A | * | 2/1998 | Gettig ......................... 604/232 |
| 6,017,331 A | * | 1/2000 | Watts et al. ................. 604/232 |

FOREIGN PATENT DOCUMENTS

EP        AU-A-603 862 A2    6/1994

* cited by examiner

*Primary Examiner*—Anthony Knight
*Assistant Examiner*—Alison K. Pickard
(74) *Attorney, Agent, or Firm*—Duane, Morris, LLP

(57) ABSTRACT

A device for sealing a syringe in which a cartridge is inserted, the cartridge being closed at its top end by a flexible membrane and being connected to an injection needle of a needle-carrier part presenting a crown between the needle and the top surface of the cartridge so as to bear against the membrane to press the membrane inwardly just inside the edge of the orifice in the top surface of the cartridge and sealing the membrane to the top surface along the edge.

4 Claims, 2 Drawing Sheets

SEALING DEVICE FOR CARPULE

The present invention relates to a sealing device intended particularly, but not exclusively, for carpules or injection cartridges, in particular those containing anesthetics.

BACKGROUND OF THE INVENTION

These cartridges, for mounting on a syringe, are constituted by a small tube, generally made of glass having an end wall that constitutes a moving piston for expelling liquid into a hollow needle. Prior to the needle being inserted, the front portion of the cartridge is closed by a rubber capsule or seal membrane disk through which the needle is to pass, the seal membrane being secured to the tube by means of a metal ring crimped over the seal membrane and onto the front of the tube.

Such a structure provides acceptable sealing during storage and transport of cartridges, with pressure being in balance on either side of the membrane. However, it is frequently observed that when pressure is applied to the end of the cartridge, once a needle has been mounted on the cartridge, then a leak occurs between the seal membrane disk and the metal ring. This leak takes place at the periphery of the rubber membrane and the metal ring. The pressure applied to the end of the carpule is transmitted by the liquid which tends to lift the membrane disk off the seat constituted by the front portion of the tube, thus allowing the liquid to pass between the seat and the rear wall of the membrane.

Proposals have already been made to improve the sealing of cartridges provided with sealing means so as to ensure that the content remains sterile.

AU-A-603 862 describes a crown that serves to center the rubber membrane.

In U.S. Pat. No. 1,993 629, a collar deforms a block of rubber that closes the front of the glass tube.

In U.S. Pat. No. 2 157 503, a collar has an acute-angled section, but neither its function nor its dimensional relationships with the tube are defined.

Those three documents relate to the hand-operated syringes, i.e. acting under relatively low pressure.

OBJECT AND SUMMARY OF THE INVENTION

The object of the invention is to mitigate the drawbacks mentioned above even when high pressure is applied, and to make injections possible without leaks, even when high pressures are necessary, e.g., for intradiploic, intraligamentary, intraseptal, intrapalatine, etc. injections. It is based on the idea that to provide sealing under high pressure it is necessary to compress a flexible membrane between the edges of two non-deformable parts.

According to the invention, in the device for sealing a syringe in which there is inserted a cartridge that is closed at its top end by a flexible membrane and that is connected to an injection needle, the link part between the needle and the front portion of the cartridge presents a projecting crown of diameter substantially equal to the diameter of the opening in the cartridge, and preferably slightly smaller than opening in the cartridge, that comes to bear against the flexible membrane so as to press it against the inside edge of the top surface of the cartridge.

Thus, when pressure is applied to the end wall of the carpule, the crown presses the disk strongly against the top edge of the opening, thereby deforming it and preventing any leakage. The connection part between the needle and the cartridge can either be an adapter for mounting the needle on a syringe or needle carrier, or else an overmolded plastic part that surrounds the needle proper. With some syringes, the needle carrier integrated in the front portion by molding can have the same disposition.

BRIEF DESCRIPTION OF THE DRAWINGS

Other characteristics and advantages of the invention will appear on reading the following description of particular embodiments, given purely by way of non-limiting example and with reference to the drawings, in which.

MORE DETAILED DESCRIPTION

Figure 1:
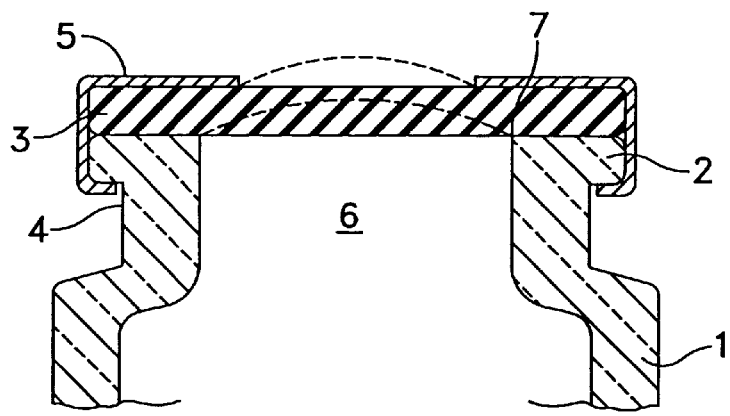
FIG. 1 is a view of the top portion of a prior art cartridge.
Figure 2:
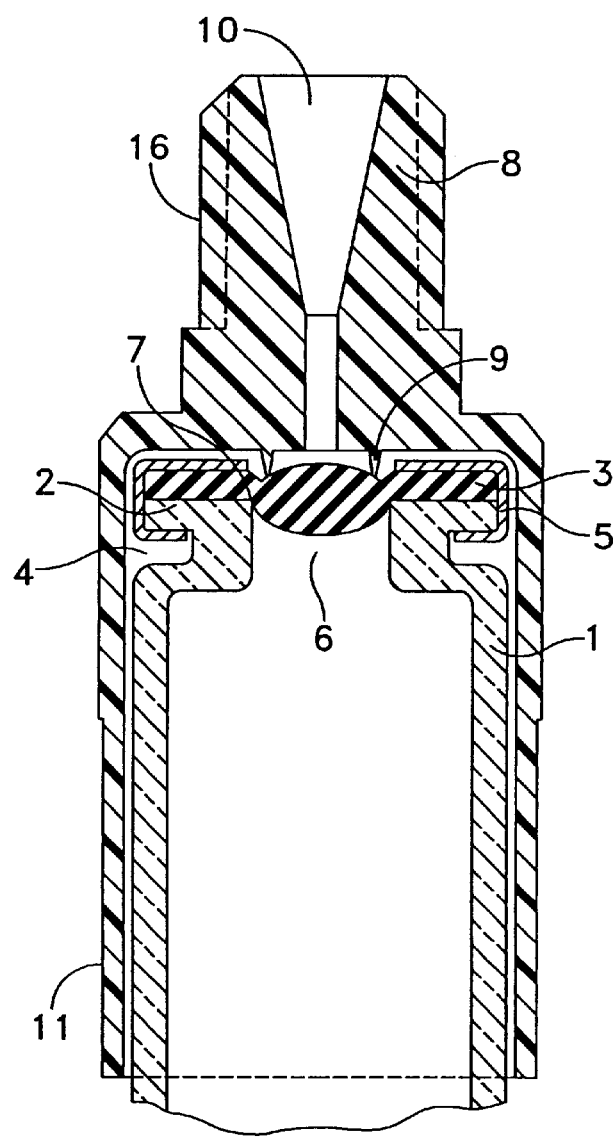
FIG. 2 is a view showing how the membrane is deformed in an injector of the invention.

FIG. 1 shows the top of a conventional type of glass cartridge 1, e.g., containing anesthetic. FIG. 2 shows the top of a glass cartridge 1 according to the invention. The cartridge 1 has a flat top surface 2 against which there rests a flexible membrane 3 of rubber, neoprene, or the like. The membrane 3 is held against the surface 2 by a metal ring 5 whose bottom portion is crimped in a groove 4 of the cartridge 1 (see also FIG. 2). As shown in FIG. 1, the top central orifice 6 of the cartridge 1 is thus closed by the membrane 3. The hollow needle (not shown in FIG. 1) passes through the membrane to take the liquid to the injection point.

When pressure is applied to the lower end wall of the cartridge (not shown) while the needle is in place, the top wall of the membrane presses firmly against the inside surface of the crimped metal ring 5, thereby tending to lift the membrane off the seat constituted by the top surface 2 of the cartridge and thus giving rise to leaks. The present invention seeks to establish a leakproof connection in the vicinity of the inner edge 7 of the top surface 2 of the cartridge around the orifice 6.

In numerous syringes, the needle is mounted in a needle carrier like the needle carrier 8 shown in FIG. 2. The needle is inserted in the needle carrier 8 to which it is generally screwed via a thread 16 and the needle carrier is slid onto the front of the syringe where it is held by friction. Sliding the needle carrier into place causes a protruding rear end of the needle to pass through the membrane 3. Reference 10 in FIG. 2 designates the passage followed by the needle proper. The bottom skirt 11 of the needle carrier preferably has indentations 12 that facilitate sliding of the needle carrier over the carpule and provide an effective mechanical connection.

Figure 3:
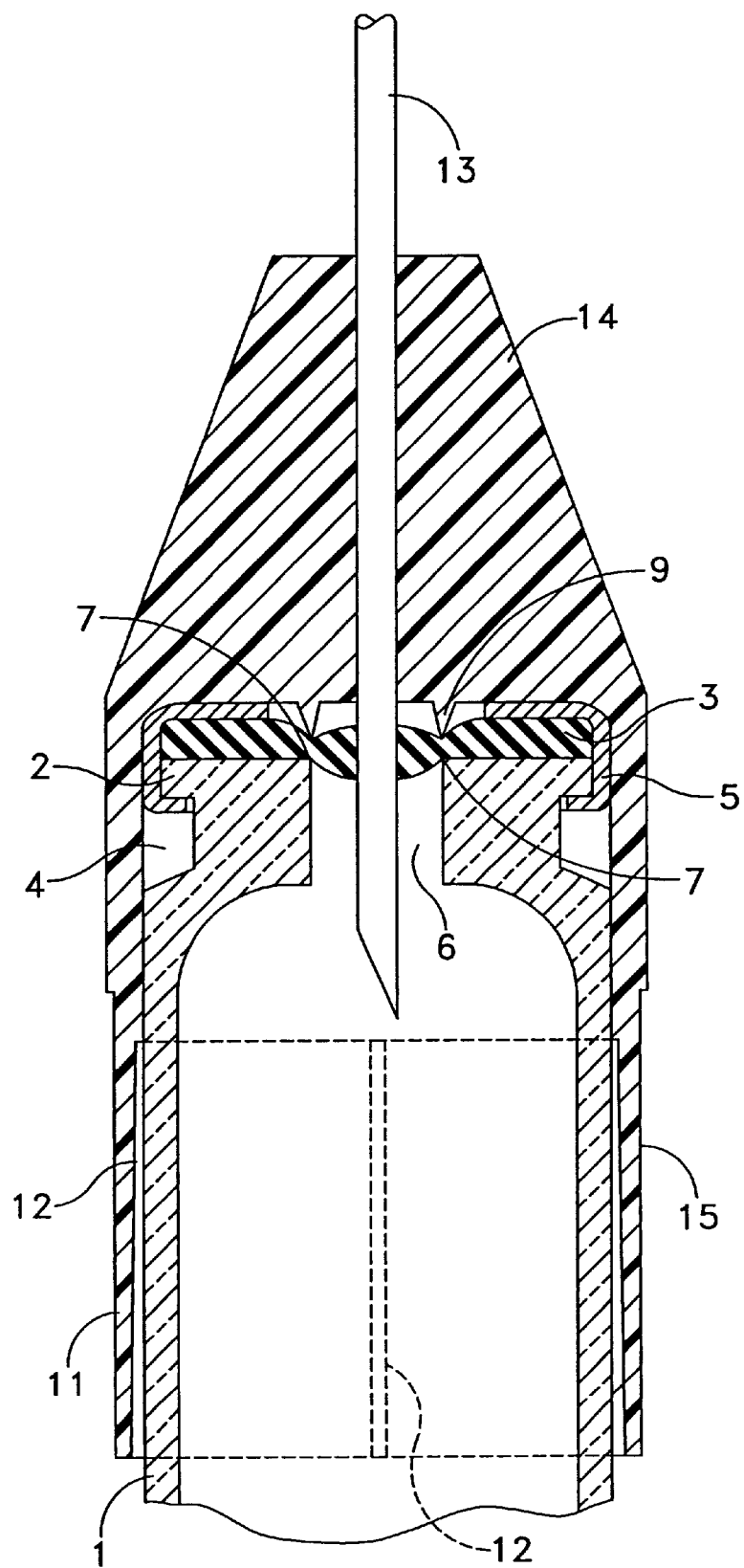
FIG. 3 is a view of a needle of the invention.

In accordance with the invention, beneath the channel 10, the needle carrier 8 has a projecting crown 9 of diameter nearly equal to the diameter of the orifice 6 of the cartridge 1 as shown in FIG. 3, or slightly smaller than the diameter of orifice 6 as shown in FIG. 2. The crown has a height that is equal to 1.5 millimeters, for example. As can be seen in FIG. 2, this sealing crown 9 bears against a same-sized zone of the membrane 3 so that prior to injection the membrane takes up the shape shown in the figure. That is to say the central portion of the membrane 3 takes up the shape of a biconvex lens. This deformation presses the membrane against the inside edge 7 of the cartridge 1 and against a ring around the inside of the top surface 2, defining orifice 6. This produces a sealing zone that opposes any leakage.

In the above embodiment, the needle is mounted on the carpule by means of a needle carrier 8. The needle proper is usually surrounded by an overmolded plastics part enabling it to be fixed in the needle carrier without there being any need to touch it with the hand. The present invention can also be implemented when the needle is mounted directly on the carpule. One such needle is shown in FIG. 3. It comprises a hollow metal channel 13 on which a plastic part 14 is overmolded. The assembly part 14 has a frustoconical front end and a slightly conical bottom skirt 15 which is provided with indentations 12 enabling the skirt 15 to slide over the outside wall of the cartridge 1. Unlike known needles, the skirt is not fitted with an inside thread as used in the preceding embodiment to secure the needle to the thread 16 of the needle carrier 8. However, the part 14 has a sealing crown 9 which performs the same function as in the preceding embodiment.

Naturally, numerous variants can be provided, in particular by substituting equivalent technical means, without thereby going beyond the ambit of the invention.

What is claimed is:

1. A syringe, comprising:

a cartridge for a liquid having a top end with a circular opening and a back end, the back end receiving a piston and the top end being closed over an edge of the circular opening by a flat flexible membrane maintained against the top end of the cartridge by a metal ring, said top end being connected to an injection needle borne by said syringe and linked to said cartridge, further comprising a projecting crown formed above the opening of said top end and projecting toward the opening in the top end of the cartridge, the crown having a diameter that is slightly smaller than a diameter around the edge of the opening, the crown bearing against said membrane to press the membrane against the edge of the opening.

2. A syringe according to claim 1, the needle being inserted in an overmolded plastic having a duct for passing the needle portion, wherein the crown is formed inside the said portion beneath the duct for passing the needle.

3. A syringe according to claim 2, wherein the said overmolded plastic portion comprises a skirt that fits around the top end of the cartridge.

4. A syringe containing a cartridge for a liquid, said cartridge having a top end and a back end, the top end having a circular central opening at which a flat flexible membrane is held by a ring around the central opening and through which part of the needle is passed, the needle being borne by a needle carrier, a projecting crown being formed on an inside and at the center of the needle carrier around the opening the crown having a diameter that is slightly smaller than a diameter around the edge of the opening, the crown bearing against said membrane to press the membrane against the edge of the opening.

* * * * *